Figure 1:
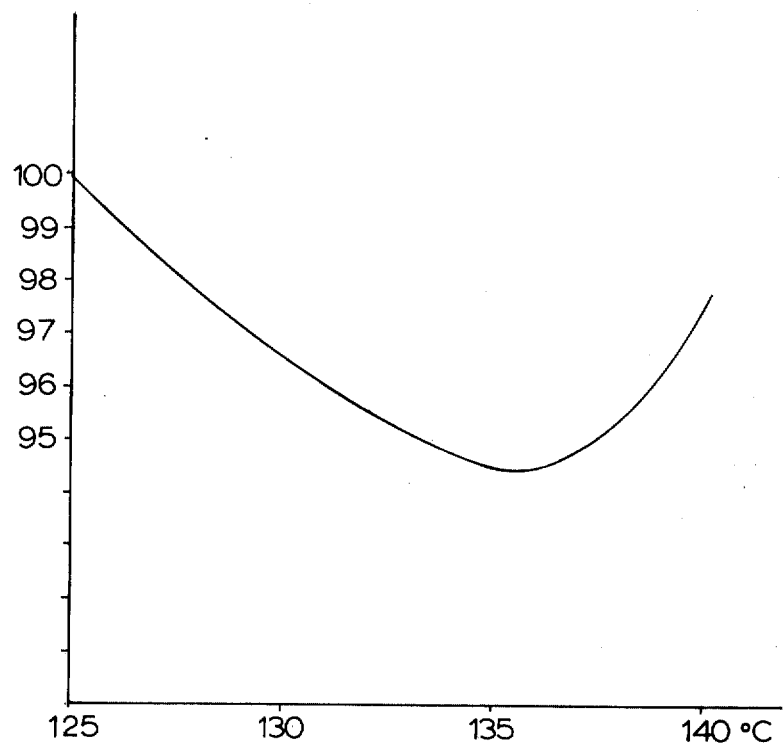

United States Patent [19]

Heunks

[11] 4,003,928
[45] Jan. 18, 1977

[54] PROCESS FOR THE PREPARATION OF UREA

[75] Inventor: Antonius M. A. Heunks, Geleen, Netherlands

[73] Assignee: Stamiarbon N.Y., Geleen, Netherlands

[22] Filed: June 24, 1974

[21] Appl. No.: 482,763

Related U.S. Application Data

[63] Continuation of Ser. No. 222,274, Jan. 31, 1972, abandoned.

[30] Foreign Application Priority Data

Feb. 3, 1971 Netherlands ............. 7101398

[52] U.S. Cl. ............................. 260/555 A
[51] Int. Cl.[2] ............................. C07C 126/00
[58] Field of Search ............. 260/555 A, 555 R

[56] References Cited

UNITED STATES PATENTS

| | | | |
|---|---|---|---|
| 3,053,891 | 9/1962 | Cook et al. | 260/555 |
| 3,172,911 | 3/1965 | Mavrovic | 260/555 |
| 3,527,799 | 9/1970 | Mavrovic | 260/555 |
| 3,759,992 | 9/1973 | Mavrovic | 260/555 |
| 3,808,271 | 4/1974 | Mavrovic | 260/555 |
| 3,816,528 | 6/1974 | Cook | 260/555 |

FOREIGN PATENTS OR APPLICATIONS 1,001,188 8/1965 United Kingdom

Primary Examiner—Oscar R. Vertiz
Assistant Examiner—Eugene T. Wheelock
Attorney, Agent, or Firm—Cushman, Darby & Cushman

[57] ABSTRACT

A process is described for the preparation of urea at a high temperature and pressure whereby the quantity of water recycled to the urea-synthesis reactor along with the recycle ammonium carbamate may be reduced. The high pressure aqueous urea solution from the reactor is expanded into two or more ammonium carbamate decomposition stages operating at successively lower pressures. In at least one of the ammonium carbamate decomposition stages the expanded aqueous urea solution is heated in a controlled manner and a first off-gas is separated. The residual aqueous urea solution is again heated and a second off-gas is removed, which off-gas is combined with the first off-gas, condensed and recycled to the urea-synthesis reactor.

4 Claims, 2 Drawing Figures

PROCESS FOR THE PREPARATION OF UREA

This is a continuation of application Ser. No. 222,274 filed Jan. 31, 1972, now abandoned.

If ammonia and carbon dioxide are reacted in a urea-synthesis reactor under conditions which are suitable for the preparation of urea, i.e., at a pressure of more than 100 atmospheres absolute and a temperature over 160° C, the reactants are first reacted to form ammonium carbamate according to the rapidly proceeding reaction:

$$2NH_3 + CO_2 \rightarrow H_2N-CO-ONH_4 \qquad (1)$$

such ammonium carbamate subsequently converting by dehydration into urea according to the reaction:

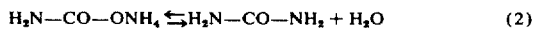

$$H_2N-CO-ONH_4 \rightleftarrows H_2N-CO-NH_2 + H_2O \qquad (2)$$

This latter reaction is an equilibrium reaction and proceeds relatively slowly compared to the ammonium carbamate forming reaction.

An aqueous urea solution is obtained from the urea-synthesis reactor containing, in addition to urea, an appreciable quantity of dissolved ammonium carbamate. Furthermore, in practice an excess quantity of ammonia is supplied to the urea-synthesis reactor, and therefore excess, unreacted ammonia will also be dissolved in this aqueous urea solution.

In order to obtain a substantially pure urea solution product, it is thus necessary to remove this dissolved ammonium carbamate and ammonia from the aqueous urea solution. This is generally accomplished in the prior art by expanding the aqueous urea solution to a lower pressure at which lower pressure at least a portion of the ammonia evaporates and at least a portion of the ammonium carbamate decomposes into gaseous ammonia and carbon dioxide. The ammonia may be further evaporated and the ammonium carbamate further decomposed by heating the aqueous urea solution. The gaseous ammonia and carbon dioxide thus liberated together with the equilibrium quantity of water vapor are then separated as an off-gas from the residual aqueous urea solution and either discharged and processed to, for instance, ammonium sulfate or ammonium nitrate, or recirculated, in part or in whole, to the urea-synthesis reactor.

The recovered ammonia and carbon dioxide are preferably recycled to the urea-synthesis reactor as an aqueous solution of ammonium carbamate since compression of an ammonia and carbon dioxide gas mixture alone involves the risk of solid ammonium carbamate depositing in, and consequently clogging, the process lines. An aqueous ammonium carbamate solution, however, can be returned to the synthesis reactor by means of a pump without a serious risk of clogging being present.

More than sufficient water to maintain the recycle ammonium carbamate in solution even under urea-synthesis pressure is generally already present as water vapor in the mixed ammonia-carbon dioxide off-gas separated from the aqueous urea solution. But as shown by reaction equation (2) above, the presence of additional water in the synthesis reactor adversely affects the conversion of ammonium carbamate into urea. The water content of the recycle ammonium carbamate solution should therefore, in principle, be only slightly in excess of that quantity of water required to maintain the recycle ammonium carbamate dissolved under urea-synthesis pressure.

It is known that the quantity of water vapor in the off-gas stream can be reduced in order to achieve an optimum water content in the ammonium carbamate recycle stream by separating and condensing this off-gas at as high a pressure as possible. Furthermore, condensing the off-gas at a high pressure has the advantage that the heat of condensation can be recovered at a high temperature level. On the other hand, the most complete evaporation of excess ammonia and decomposition of unconverted ammonium carbamate is obtained at a low pressure level after a large pressure reduction of the aqueous urea solution.

These conflicting objectives have been partially satisfied in the known urea preparation process wherein the aqueous urea solution is expanded in two or more successively lower pressure stages. In each of such pressure stages, the expanded urea solution is first heated to further decompose ammonium carbamate after which the gases liberated by the expansion and heating are separated from the aqueous urea solution as an off-gas containing ammonia, carbon dioxide and water vapor, which off-gas is condensed in the ammonium carbamate solution obtained in the next lower pressure stage. Generally in such processes, a major portion of the excess ammonia is separated from the first pressure stage off-gas and condensed separately. By this mode of decomposition and condensation an appreciable reduction in the water content of the off-gases can be obtained, resulting in a lower water content of the ammonium carbamate solution to be recycled from the first pressure stage to the synthesis reactor.

It is further known from U.S. patent application Ser. No. 547,116, filed Mar. 23, 1966, that the water content of the off-gas streams from one or more of these pressure stages in a multi-stage recycle system can be further reduced by first adiabatically expanding the aqueous urea solution and separating a first off-gas stream consisting primarily of the gases liberated during the adiabatic expansion, heating the residual aqueous urea solution after the first separation, separating a second off-gas from the heated aqueous urea solution, and combining and condensing the first and second off-gas streams for recycle to the next higher pressure stage. Such a process has already been successfully applied on an extensive scale.

Applicant has now surprisingly found that a combined off-gas mixture with an even lower water vapor content can be obtained, improving upon the process of U.S. application Ser. No. 547,116, if a controlled amount of heat is added to the expanded aqueous urea solution in a preliminary heating step prior to the first gas-liquid separation in one or more of the pressure stages. Applicant has found that if heat is applied to the expanded aqueous urea solution prior to the first gas-liquid separation, and if the residual aqueous urea solution is heated to the same temperature as that attained in the prior art and a second off-gas is separated, the total water content of the combined first and second gas-liquid separation off-gases will first gradually decrease, reach a minimum value, and again increase as the total amount of heat supplied prior to such first gas-liquid separation is increased.

FIG. 1 is a graph showing the effect of the addition of heat in a preliminary heating step on the water content of the combined off-gas streams.

Figure 2:
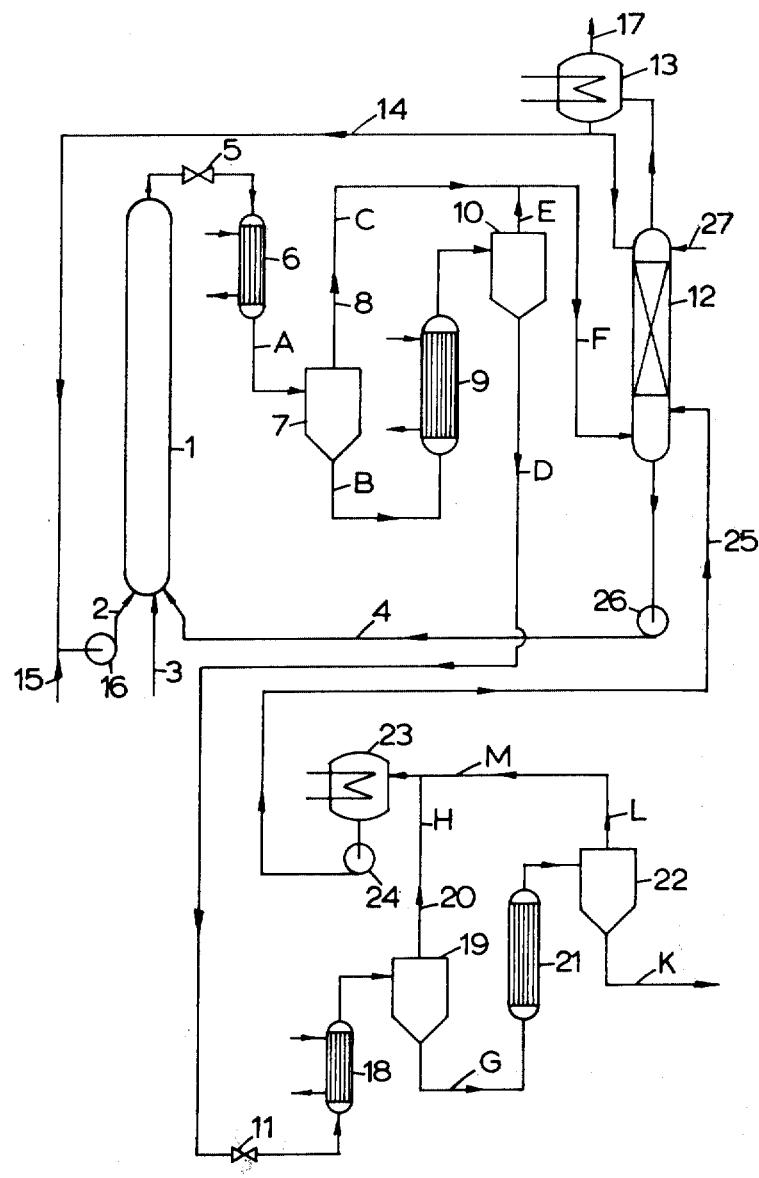

FIG. 2 schematically illustrates a preferred embodiment of the invention.

In FIG. 1, the water content of the combined off-gas streams of the first pressure stage has been plotted against the quantity of heat supplied to the preliminary heater prior to the first gas-liquid separation in such pressure stage, the quantity of heat added being indicated by the solution temperature prior to the first separation.

In plotting this graph of FIG. 1, an aqueous urea solution with a given composition was expanded adiabatically from 200 atmospheres absolute to 18 atmospheres absolute. The adiabatic equilibrium temperature of the aqueous urea solution after this expansion to 18 atmospheres absolute was found to be 125° C. The water content of the combined off-gas stream obtained without the addition of heat between the expansion and the first gas-liquid separation amounted to 4788 kmoles/day, which was assigned the arbitrary value of 100 % based on the total quantity of aqueous urea solution entering such pressure stage. As the amount of heat added by the preliminary heater was increased, the total water content of the combined off-gas stream decreased, and at a solution temperature of 135° C amounted to 4526 kmoles/day, being 94.5 % of the quantity attainable without the preliminary heating. With the further addition of heat, the water content reached a minimum at 94.4 % after which the water vapor content increased again quite rapidly.

Based on the above finding, a process has been developed wherein the water content of the ammonium carbamate recycle stream to the urea-synthesis reactor can be reduced even below that now attained by the currently used prior art process. Accordingly, the improvement of this invention applies to a process for the preparation of urea having at least three pressure levels or stages. In the first and highest pressure stage, ammonia, carbon dioxide and recycled ammonium carbamate are reacted in a urea-synthesis reactor at a pressure of at least 160 atmospheres absolute and at a temperature of at least 160° C. The ammonia and carbon dioxide are fed to the urea-synthesis reactor in an overall molar ratio of 3 to 5 parts ammonia to one part carbon dioxide, this overall molar ratio taking into account, the recycled ammonia, the ammonia and carbon dioxide bound in the recycled ammonium carbamate, as well as the fresh ammonia and carbon dioxide feed.

The aqueous urea solution leaving the urea-synthesis pressure stage, which in addition to urea, contains ammonium carbamate and excess unreacted ammonia, is then led through at least two ammonium carbamate decomposition stages at successively lower pressure levels wherein the ammonia carbamate and excess ammonia are removed from the aqueous urea solution and prepared for recycle to the urea-synthesis reactor.

Each of these ammonium carbamate decomposition pressure stages includes the steps of expanding the aqueous urea solution from the next higher pressure stage through an expansion valve, followed by a first separation of an off-gas comprising ammonia, carbon dioxide and water vapor. The expansion of this aqueous urea solution, which is substantially adiabatic, will effect a partial decomposition of the ammonium carbamate into ammonia and carbon dioxide, and a partial evaporation of the excess ammonia, the heat required for this decomposition and evaporation being supplied by the latent heat of the aqueous urea solution itself, resulting in a decrease in the solution temperature over the expansion. The lower temperature thus attained after the expansion is complete, and the phases are in equilibrium, will be called herein the adiabatic equilibrium temperature of the expanded aqueous urea solution.

Subsequent to the first separation, the residual aqueous urea solution is heated to further decompose ammonium carbamate and passed into a second separation wherein a second off-gas of ammonia, carbon dioxide, and water vapor is taken off leaving an aqueous urea solution having a reduced ammonium carbamate and reduced excess ammonia content.

The advantageous reduced recycle water content of the present invention is attained by including within one or more of the ammonium carbamate decomposition pressure stages a preliminary heating step after the expansion and prior to the first separation. The heat input to this preliminary heating step is controlled so as to increase the temperature of the expanded aqueous urea solution by no more than 20° C. above the adiabatic equilibrium temperature of that aqueous urea solution. The heat input to this preliminary heating step is further controlled, as well as the heat input to the heater subsequent to the first separation, so that the temperature increase of the aqueous urea solution due to the preliminary heater constitutes no more than 40% of the total temperature rise in that particular pressure stage subsequent to the expansion.

The improved process of this invention is further elucidated in the simplified process diagram of FIG. 2.

Synthesis reactor 1, preferably operating at a pressure of 175–210 atmos. absolute and a temperature of 180°–200° C, is supplied via line 2 with liquid ammonia and via line 3 with gaseous carbon dioxide. Additionally, a recycled ammonium carbamate solution is introduced into the reactor through line 4. The gross molar ratio between ammonia and carbon dioxide, in which the ammonium carbamate is considered as ammonia and carbon dioxide, amounts to, for example, 3.5 or 4 to 1.

In the reactor an aqueous solution of urea is formed, which also contains unconverted ammonium carbamate, excess ammonia, and a small amount of gaseous inert components. This urea-synthesis solution is expanded adiabatically to a pressure of, for instance, 18–20 atmos. absolute through reducing valve 5 as a result of which a major part of the excess ammonia evaporates and part of the ammonium carbamate dissociates. The heat required for this purpose is withdrawn from the solution proper, which results in a decrease of the aqueous urea solution temperature to 120°–125° C. The gas-liquid mixture (A) so formed is led through heat exchanger 6, where steam is used to increase the temperature to 127°–140° C, thereby further decomposing ammonium carbamate and further evaporating ammonia and carbon dioxide. Water is also evaporated, but due to the relatively small heat input, the quantity of water vapor is kept relatively small.

In separator 7, a first off-gas (C) is separated from the gas-liquid mixture leaving heat exchanger 6, which off-gas contains, besides ammonia, carbon dioxide and water vapor, the gaseous inert components. This first off-gas is discharged from separator 7 via line 8. The residual aqueous urea solution (B) is heated in heat exchanger 9 to a temperature of 150°–170° C at which temperature a major part of the ammonium carbamate still present in the solution is decomposed. The gas-liquid mixture leaving heat exchanger 9 is led to gas-liquid separator 10 where a second off-gas (E) containing ammonia, carbon dioxide and water vapor is separated from the aqueous urea solution. This second off-gas (E) is combined with the first off-gas (C) and the combined off-gas (F) is led into the absorption-condensation column 12, which column is also supplied with the colder ammonium carbamate solution formed in the subsequent lower pressure stage.

In absorption-condensation column 12, part of the ammonia and carbon dioxide present in the combined off-gas stream, as well as the water vapor, condenses to form an aqueous ammonium carbamate solution. The excess ammonia ascends column 12 and, with the aid of liquid ammonia reflux from ammonia condenser 13 and a small quantity of water supplied via line 27, is substantially freed of carbon dioxide. The ammonia, together with the inert components, is led into condenser 13 where the ammonia condenses and is, in part, returned as reflux to column 12, while the remainder, together with the fresh ammonia supplied via line 15, is led via line 14 into synthesis reactor 1 by means of pump 16. The non-condensable inert gases leave condenser 13 via line 17.

The aqueous urea solution (D) coming from separator 10, which is now reduced in excess ammonia and carbon dioxide content, is further expanded through reducing valve 11 and an adiabatic equilibrium temperature of, for example, 120° C is attained. This expanded aqueous urea solution is then led to heat exchanger 18 where the solution temperature is increased to 127°–135° C. This results in the dissociation of part of the ammonium carbamate still present after the second expansion, again liberating gaseous ammonia, carbon dioxide and water vapor. A first off-gas (H) is separated in separator 19 from the aqueous urea solution at the lower pressure and discharged via line 20. The residual aqueous urea solution (G) is led from separator 19 into heat exchanger 21, where it is heated to 145°–160° C, at which temperature and lower pressure, the ammonium carbamate still present substantially completely decomposes. A second low-pressure off-gas (L), consisting of ammonia, carbon dioxide and water vapor, is removed in gas-liquid separator 22, leaving an aqueous urea solution (K) which is virtually free of ammonium carbamate. After expanding this aqueous urea solution (K) to atmospheric pressure, it is processed in an evaporation or crystallization section not shown in FIG. 2.

As in the first ammonium carbamate decomposition stage, the first and second off-gas flows are combined, and the combined off-gas stream (M) is led into condenser 23 where total condensation takes place. The ammonium carbamate solution thus formed is pumped via line 25 into the bottom section of absorption-condensation column 12 by means of pump 24 and, together with the ammonium carbamate solution formed in column 12, is returned via line 4 to urea-synthesis reactor 1 with the aid of pump 26.

To further illustrate the invention, the following example is given in which a urea synthesis according to the prior art process of U.S. application Ser. No. 547,166 described above is compared to the improved urea-synthesis process of this invention.

The process line conditions and compositions are given in Tables I and II, the identification of process lines being keyed into the process line designations on FIG. 2. Table I gives the conditions and compositions in the first ammonium carbamate decomposition pressure stage, and Table II gives the conditions and compositions in the second ammonium carbamate decomposition pressure stage. In each of the tables, the entries in column $a$ apply to the prior art process; in column $b$ to the process according to this invention wherein a preliminary heater is employed only in the first ammonium carbamate decomposition pressure stage; and in column $c$ to the process according to this invention wherein a preliminary heater is included in both the first and second ammonium carbamate decomposition stages.

The comparison was made in a urea plant having a production capacity of 500 tons/day, in which the urea-synthesis reaction took place at a pressure of 200 atmos. absolute, a temperature of 190° C and a gross molar $NH_3/CO_2$ ratio of 4 to 1. In the first stage, the urea-synthesis solution was expanded to 18 atmos. absolute, whereupon the adiabatic equilibrium temperature was 125° C.

The expanded urea solution (A) was first heated to 135° C in preliminary heat exchanger 6, and the residual aqueous urea solution (B) was heated in heat exchanger 9 to 160° C.

In the second stage, the aqueous urea solution (D) from separator 10 was expanded to a pressure of 4 atmos. absolute resulting in an adiabatic equilibrium temperature of 123° C. The residual aqueous urea solution (G), after the first separation at the lower pressure, was heated to 150° C in heat exchanger 21. For the figures in column $c$ of both tables where a preliminary heater was also employed in the second ammonium carbamate decomposition pressure stage, the aqueous urea solution (D), after expansion was heated to 130° C in preliminary heat exchanger 18 prior to the first gas-liquid separation.

The tables show that if the preliminary heater and appropriate conditions of the invention are applied only in the first ammonium carbamate decomposition pressure stage, an off-gas flow (F) will be obtained which contains 262 kmoles of $H_2O$/day (or 5.5%) less than will be obtained with the prior art process. With the inclusion of the preliminary heater and appropriate conditions of the invention in both ammonium carbamate decomposition pressure stages, the reduction of the water quantity in the off-gas flow (F) will be 319 kmoles/day (or 6.7%) from the prior art.

Table I

| Flow | Component | a | b | c |
|---|---|---|---|---|
| A | Urea | 8470 | 8470 | 8470 |
| $p = 18$ ats abs. | $CO_2$ | 5191 | 5104 | 4974 |
| $t = 125°$ C | $NH_3$ | 37704 | 37356 | 36836 |
|  | $H_2O$ | 18419 | 18128 | 17692 |
| B | Urea | 8470 | 8470 | 8470 |
| $p = 18$ ats abs. | $CO_2$ | 4425 | 3050 | 3050 |
| $t_a = 125°$ C | $NH_3$ | 16500 | 10775 | 10775 |
| $t_{b,c} = 135°$ C | $H_2O$ | 17156 | 15628 | 15249 |
| C |  | $CO_2$ | 766 | 2054 | 1924 |
| $p = 18$ ats abs. | $NH_3$ | 21204 | 26581 | 26061 |
| $t_a = 125°$ C | $H_2O$ | 1263 | 2500 | 2443 |
| $t_{b,c} = 135°$ C |  |  |  |  |
| D | Urea | 8470 | 8470 | 8470 |
| $p = 18$ ats abs. | $CO_2$ | 510 | 510 | 510 |
| $t = 160°$ C | $NH_3$ | 3720 | 3720 | 3720 |
|  | $H_2O$ | 13631 | 13602 | 13223 |
| E |  | $CO_2$ | 3915 | 2540 | 2540 |
| $p = 18$ ats abs. | $NH_3$ | 12780 | 7055 | 7055 |
| $t = 160°$ C | $H_2O$ | 3525 | 2026 | 2026 |

Table I-continued

| Flow | Component | a | b | c |
|---|---|---|---|---|
| F = C + E | $CO_2$ | 4681 | 4594 | 4464 |
| | $NH_3$ | 33984 | 33636 | 33116 |
| | $H_2O$ | 4788 | 4526 | 4469 |

Table II

| Flow | Component | a | b | c |
|---|---|---|---|---|
| G | Urea | 8470 | 8470 | 8470 |
| p = 4 ats abs. | $CO_2$ | 390 | 390 | 250 |
| $t_{a,b} = 123°$ C | $NH_3$ | 1690 | 1690 | 1115 |
| $t_c = 130°$ C | $H_2O$ | 12741 | 12712 | 11598 |
| H | $CO_2$ | 120 | 120 | 260 |
| p = 4 ats abs. | $NH_3$ | 2030 | 2030 | 2605 |
| $t_{a,b} = 123°$ C | $H_2O$ | 890 | 890 | 1625 |
| $t_c = 130°$ C | | | | |
| K | Urea | 8470 | 8470 | 8470 |
| p = 4 ats abs. | $CO_2$ | 85 | 85 | 85 |
| t = 150° C | $NH_3$ | 345 | 345 | 345 |
| | $H_2O$ | 10270 | 10241 | 10198 |
| L | $CO_2$ | 305 | 305 | 165 |
| p = 4 ats abs. | $NH_3$ | 1345 | 1345 | 770 |
| t = 150° C | $H_2O$ | 4271 | 2471 | 1400 |
| M = H + L | $CO_2$ | 425 | 425 | 425 |
| | $NH_3$ | 3375 | 3375 | 3375 |
| | $H_2O$ | 3361 | 3361 | 3025 |

Application of the invention in the first and second stages results in the quantity of $H_2O$/day separated off in the off-gas flow (M), in the second stage, being reduced by 336 kmoles. In this case, moreover, the supply of $H_2O$ via line 27 to absorption-condensation column 12 can be reduced by 72 kmoles/day. The amount of water recycled to the synthesis reactor will then be reduced by 319 + 336 + 72 + 727 kmoles/day, or 5.5%, in total. This will cause the conversion, calculated on the basis of the quantity of carbon dioxide supplied to the synthesis reactor, to be increased by 1%. As a result, the steam consumption decreases by 70 kg per ton of urea produced, which amounts to approximately 7% of the total steam consumption in the two stages.

What is claimed is:

1. In a process for the preparation of urea having at least three successively lower pressure stages comprising:

a urea-synthesis pressure stage wherein ammonia and carbon dioxide together with recycled ammonium carbamate are fed into a urea-synthesis reactor in an overall ammonia to carbon dioxide ratio of 3-5 to 1 and reacted at a pressure of at least 160 atmos. absolute and at a temperature of at least 160° C thereby forming an aqueous urea solution, said aqueous urea solution also containing ammonium carbamate and excess ammonia; and at least two ammonium carbamate decomposition pressure stages wherein the aqueous urea solution from the next higher pressure stage is reduced in ammonium carbamate and excess ammonia content, each of such ammonium carbamate decomposition pressure stages having the process steps including:

the adiabatic expansion of said aqueous urea solution from the next higher pressure stage thereby decomposing ammonium carbamate, a first separation wherein the expanded aqueous urea solution is separated into a first off-gas stream and a residual aqueous urea solution, heating said residual aqueous urea solution thereby further decomposing ammonium carbamate, a second separation wherein said heated residual aqueous urea solution is separated into a second off-gas stream and an aqueous urea solution reduced in ammonium carbamate content, combining said first and said second off-gas streams into a combined off-gas stream, and condensing and recycling said combined off-gas stream to the next higher pressure stage, the improvement consisting essentially in including in at least one of said ammonium carbamate decomposition pressure stages, the step of preliminary heating of said expanded aqueous urea solution prior to said first separation, so as to increase the temperature of said expanded aqueous urea solution to no more than 20° C above the temperature of said expanded aqueous urea solution, said temperature increase further constituting no more than 40% of the total temperature increase in said at least one of said ammonium decomposition pressure stages subsequent to said expansion.

2. In the process of claim 1 wherein the aqueous urea solution entering the first of said at least two ammonium carbamate decomposition pressure stages is expanded to a pressure of 15 to 30 atmos. absolute, and wherein the residual aqueous urea solution subsequent to said first separation in such stage is heated to a temperature of 150°-170° C, the further improvement comprising heating said expanded aqueous urea solution in said preliminary heating step to a temperature of 7°-15° C above the temperature of said expanded aqueous urea solution subsequent to said expansion.

3. In the process of claim 1 wherein said aqueous urea solution is expanded in the second of said at least two ammonium carbamate decomposition pressure stages to a pressure of 2 to 5 atmos. absolute and the residual aqueous urea solution subsequent to the separation of said first off-gas stream is heated to a temperature of 145°-160° C, the further improvement comprising heating said expanded aqueous urea solution in said preliminary heating step to a temperature of 7°-15° C above the temperature of said expanded aqueous urea solution subsequent to said expansion.

4. In the process of claim 2 wherein said aqueous urea solution is expanded in the second of said at least two ammonium carbamate decomposition pressure stages to a pressure of 2 to 5 atmos. absolute and the residual aqueous urea solution subsequent to the separation of said first off-gas stream is heated to a temperature of 145°-160° C, the further improvement comprising heating said expanded aqueous urea solution in said preliminary heating step to a temperature of 7°-15° C above the temperature of said expanded aqueous urea solution subsequent to said expansion.

* * * * *